United States Patent [19]
Bureau et al.

[11] Patent Number: 5,840,257
[45] Date of Patent: Nov. 24, 1998

[54] DEVICE FOR USE WITH AN OIL LAMP TO ALLOW DIFFUSION OF THE SCENT OF A PERFUME

[75] Inventors: Jean-Louis Bureau, Charlesbourg; Jacques Bureau, Ste-Anne de Beaupré, both of Canada

[73] Assignee: Rayflam Inc., Sainte-Foy, Canada

[21] Appl. No.: 854,389

[22] Filed: May 12, 1997

Related U.S. Application Data

[60] Provisional application No. 60/017,593, May 14, 1996, and provisional application No. 60/037,544, Feb. 11, 1997.

[30] Foreign Application Priority Data

Apr. 8, 1997 [CA] Canada ................................. 2202179

[51] Int. Cl.[6] ...................................................... A62B 7/08
[52] U.S. Cl. ......................... 422/125; 422/305; 422/126; 431/320
[58] Field of Search ................................. 422/305, 125, 422/126; 431/320

[56] References Cited

U.S. PATENT DOCUMENTS

| 651,100 | 6/1900 | Blakely | 422/126 |
|---|---|---|---|
| 2,023,402 | 12/1935 | Brown | 422/126 |
| 3,321,938 | 5/1967 | Bureau . | |
| 3,355,913 | 12/1967 | Frangos | 422/125 |
| 4,781,895 | 11/1988 | Spector | 422/125 |

FOREIGN PATENT DOCUMENTS

| 2693788 | 6/1992 | France . |
|---|---|---|
| 2080514 | 7/1981 | United Kingdom . |
| 2139342 | 4/1984 | United Kingdom . |

*Primary Examiner*—Carroll B. Dority
*Attorney, Agent, or Firm*—Robic

[57] ABSTRACT

A device for use with an oil lamp to allow the diffusion of the scent of a perfume. The device has a circular vessel and a central tubular element extending longitudinally through the center of the vessel. A wick is inserted through the central tubular element. The vessel is closed at the bottom and open at the top, defining a perfume-holding area. In a first and second embodiment, the device also has an outwardly projecting lip along the circumference of the vessel at the top thereof. In a third embodiment, the vessel has a diameter that is greater than the diameter of the opening of the oil lamp, and is provided with a resilient member at the bottom of the central tubular element. In use, a user pours a given amount of perfume in the perfume-holding area. The device is then placed on the lip of the oil lamp and over the opening and the wick is lit. The heat generated by the flame of the wick heats the device, which in turns heats the perfume, thereby releasing a pleasing smell.

28 Claims, 8 Drawing Sheets

DEVICE FOR USE WITH AN OIL LAMP TO ALLOW DIFFUSION OF THE SCENT OF A PERFUME

This is a provisional application of Ser. No. 60/017,593, filed May 14, 1996. Also this is a provisional application of Ser. No. 60/037,544, filed Feb. 11, 1997.

FIELD OF THE INVENTION

The invention is concerned with a device for use with an oil lamp to allow diffusion of the scent of a perfume. The invention is also concerned with the combination of an oil lamp with such a device.

DESCRIPTION OF THE PRIOR ART

Conventionally, oil lamps comprise a glass bottle, at the neck of which is inserted an oil burner head which holds a wick. The oil burner head may include a mechanism to adjust the length of the wick and thus the intensity of the flame, or may include a mechanism to hold the wick in place at a predetermined length without requiring adjustment. Reference may be made to U.S. Pat. No. 3,321,938 (equivalent to Canadian patent no. 789,795) for such a mechanism, which discloses an oil burner head having a glass tube through which a wick projects. The oil burner head rests on the lip of the oil lamp.

The glass bottle is filled with oil or liquid paraffin. The oil or liquid paraffin can be perfumed, to provide a pleasing smell when the lamp is lit. However, due to the fact that the oil burner head is inserted inside the glass bottle and that there is no space between the neck of the glass bottle and the oil burner head, the perfume in the oil or liquid paraffin is burned at the same time as the paraffin and thus no odor is released, or if any odor at all, that of burnt perfume.

Thus, it may be advantageous to use a device which leaves a space between the lip of the glass bottle and the oil burner head, so that there is uninterrupted air flow between the inside of the glass bottle and the ambient air. Reference may be made to our co-pending application no. 08/680.862, now U.S. Pat. No. 5,669,767, for such a device, the contents of which are incorporated herewith by reference.

However, once the bottle is filled with perfumed oil or liquid paraffin, the quantities are such that the lamp will burn for a long time before additional oil is required. Thus, should a user wish to change the scent of the oil or desire no scent released at all, they must wait until the oil or paraffin is completely burned before being able to change the perfume or fill the glass bottle with unscented oil or liquid paraffin.

SUMMARY OF THE INVENTION

An object of the invention is to provide a device into which perfume may be poured to permit the odor of the perfume to be released in the ambient air without being burned or mixed with the oil or liquid paraffin.

In accordance with the invention, this object is achieved with a device comprising a circular vessel having a top and a bottom and a central tubular element extending longitudinally through the center of the vessel through which a wick projects. The vessel is closed at the bottom thereof and open at the top, defining a perfume-holding area. The device also includes means to hold in position the device on the lip of an oil lamp or bottle and over its opening.

In use, a desired quantity of perfume is poured into the perfume-holding area of the device, and the device is then placed on the lip of the oil lamp and over the opening. Alternatively, a desired quantity of perfume is poured in the perfume-holding area of the device once the device is placed on the lip of the oil lamp and over the opening. When the wick is lit, the heat generated by the flame heats the device, which, in turn, heats the perfume thereby releasing a pleasing smell.

Another object of the invention is to provide for the combination of the device and an oil lamp to allow diffusion of the scent of a perfume.

BRIEF DESCRIPTION OF THE DRAWINGS

The present invention and its advantages will be more easily understood after reading the following non-restrictive description of preferred embodiments thereof, made with reference to the following drawings where the same numeral designates the same feature in all of the drawings, and.

DESCRIPTION OF PREFERRED EMBODIMENTS OF THE INVENTION

Figure 1:
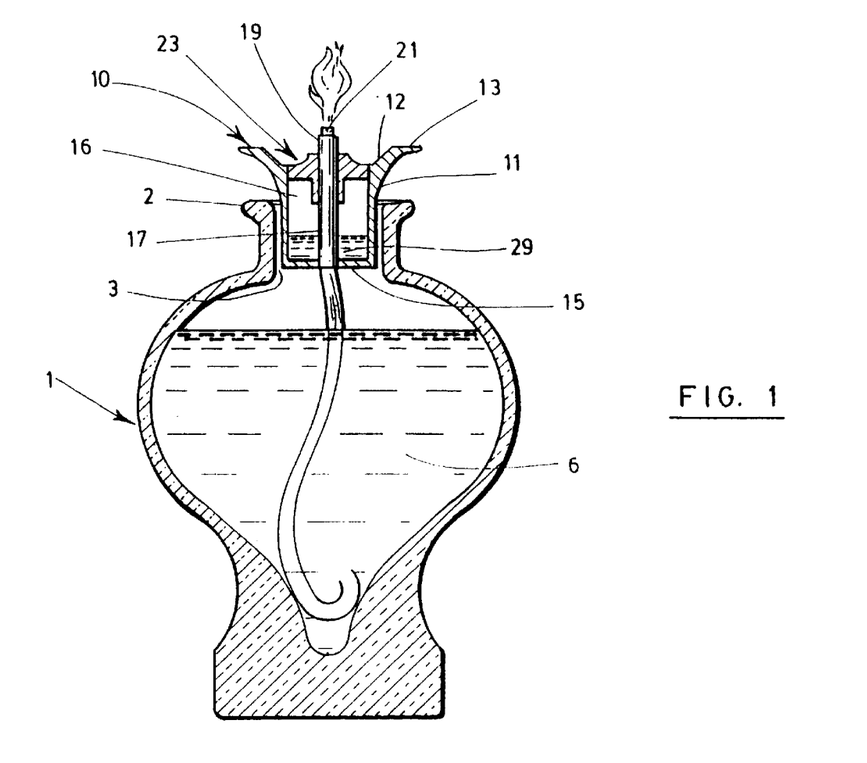
FIG. 1 is a cross-sectional view of an oil lamp including a device according a first preferred embodiment of the invention.

FIG. 1 shows a glass bottle 1, having a lip 2 and an opening 3, filled with oil or liquid paraffin 6 and including a device 10 according to a first preferred embodiment of the invention, placed on the lip 2 of the glass bottle 1. It should be understood throughout this description that glass bottle 1 means an oil lamp and includes any type of container into which oil or liquid paraffin may be poured, as will hereinafter be explained. Furthermore, the container does not have to be made of glass, and could be made of any other material suitable for use as an oil lamp. In the following description, bottle and oil lamp are used interchangeably.

Figure 2:
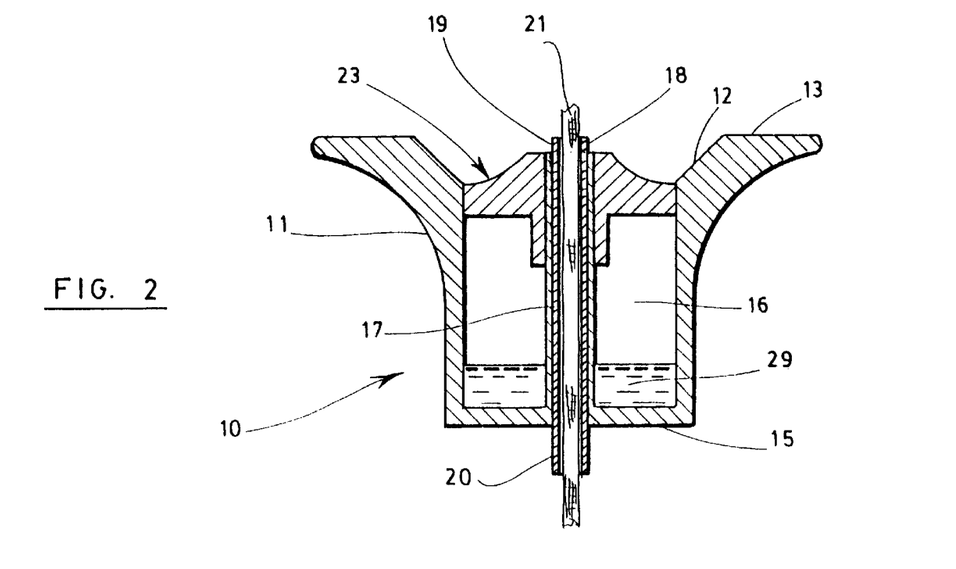
FIG. 2 is a cross-sectional view of the device of FIG. 1.

The device 10 comprises a circular vessel 11 having a top 12 and a bottom 15 and an outwardly projecting lip 13 along the circumference of the vessel 11 at the top 12 thereof. However, it should be understood that any means to hold the device 11 in place on the lip of the bottle are acceptable. For example, the vessel could be provided with a plurality of extensions at the periphery thereof which would rest on the lip of the bottle.

The vessel 11, according to this first embodiment, extends downwardly into the opening 3 of the bottle 1 and is closed at the bottom 15 thereof and open at the top 12, defining a perfume-holding area 16. The device 10 also comprises a central tubular element 17 having a top 18 and a bottom 20, preferably made of metal, extending longitudinally through the center of the vessel 11 through which a wick 21 is inserted. A wick-supporting tube 19 can also be inserted through the central tubular element 17 to hold the wick 21 in position.

A ring-shaped element 23 having a central opening 25 is placed around the central tubular element 17 near the top 18 thereof and at the top 12 of the vessel 11 so that the wick 21 projects upwardly by a given distance. The ring-shaped element 23 has a diameter slightly larger than the inside diameter of the vessel 10 such that once it is placed around the longitudinal tubular element 17, the ring-shaped element 23 rests at the top end of the vessel 10 as shown on FIGS. 1 and 2. The ring-shaped element 23 is provided with a plurality of openings 27 at the periphery 26 thereof to permit air flow between the perfume-holding area 16 and the ambient air, as better shown on FIG. 3.

Figure 3:
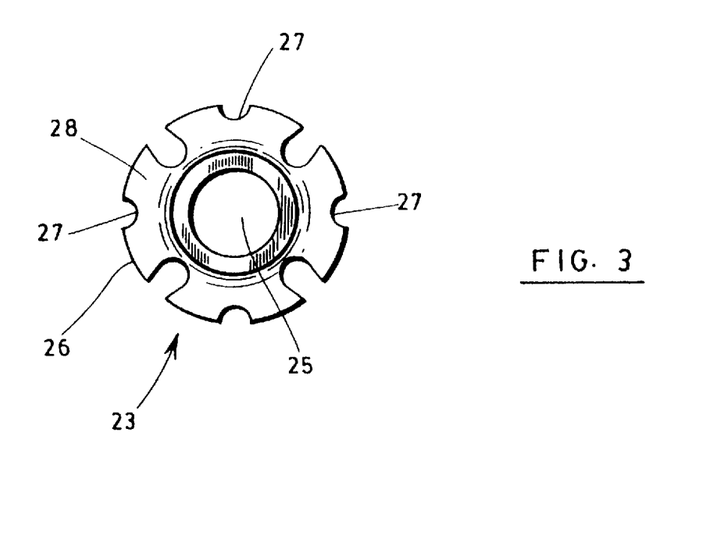
FIG. 3 is a top plan view of a ring-shaped element for use with the device of FIG. 1.
Figure 4:
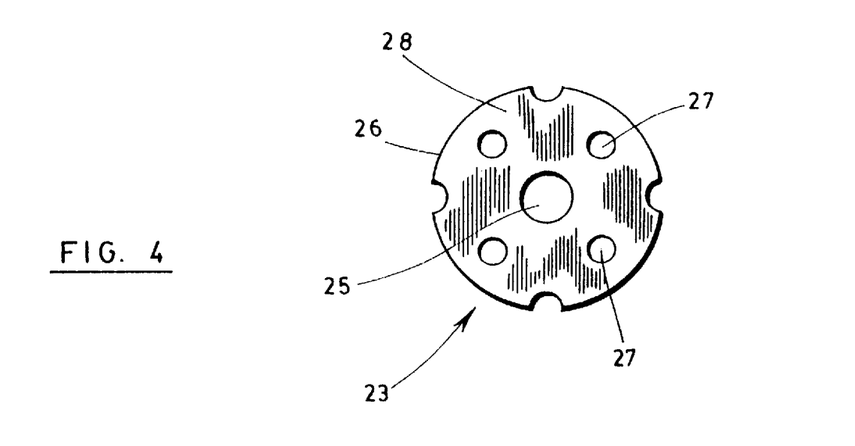
FIG. 4 is a top plan view of another ring-shaped element for use with the device of FIG. 1.

Preferably, the openings 27 are generally semi-circular as shown on FIG. 3 and located at the periphery 26 of the ring-shaped element 23, but any other form of opening 27 at the periphery 26 or in the body 28 itself of the ring-shaped element 23 is acceptable, provided the openings 27 are sufficient to permit uninterrupted air flow between the perfume holding area 16 and the ambient air. For example, see FIG. 4 for another configuration for the openings 27 of the ring-shaped element 23.

In use, the ring-shaped element 23 is removed from the device 10 which is then filled with perfume 29 in an amount determined by a user. The ring-shaped element 23 is re-placed on the device 10 around the longitudinal tubular element 17. The device 10, now filled with perfume, is then placed on the lip 2 of the glass bottle 1. When the wick 21 is lit, the heat generated by the flame heats the device 10, which, in turn, heats the perfume 29 thereby releasing a pleasing smell through the openings 27 of the ring-shaped element 23.

Thus, given the perfume-holding area 16, any number of perfumes may be poured into it to provide a pleasing smell. Furthermore, since the perfume is not mixed with the oil or liquid parrafin, the contents of the vessel 11 may be discarded and replaced with a different perfume should a user so wish. The device also presents the additional advantage of not burning the perfume at the same time that the wick is lit. The pleasing smell is released only by the heat generated by the flame, through convection and diffusion.

Preferably, the vessel 11 and the ring-shaped element 23 are made of brass to permit adequate heat conductivity. The vessel 11 preferably has a height of approximately 35 mm and an outside diameter of approximately 20 mm. Thus, the device may only be installed on oil lamps having an opening larger than 20 mm.

Figure 5:
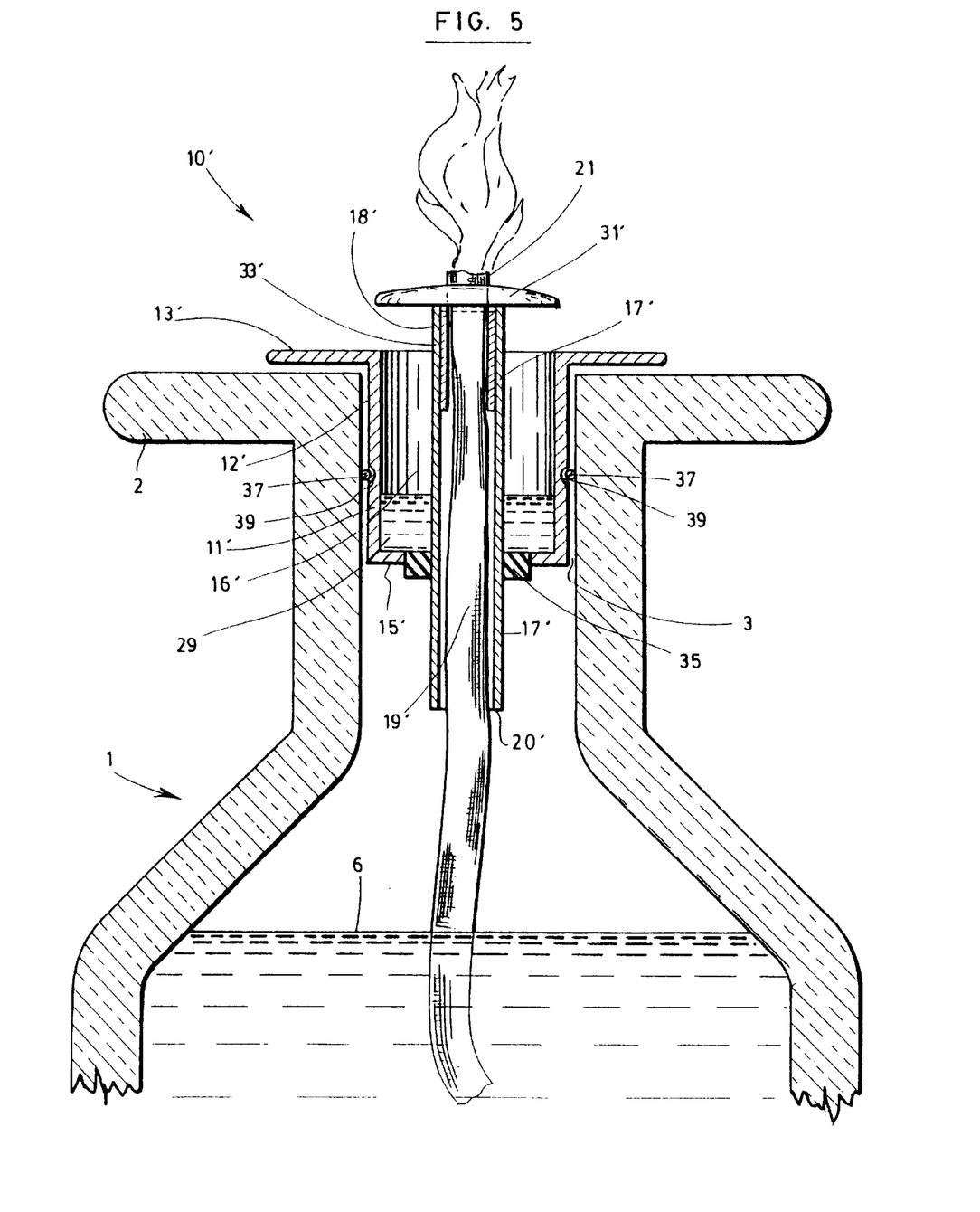
FIG. 5 is a cross-sectional view of a device according to a second preferred embodiment of the invention.

FIG. 5 shows a glass bottle 1, having a lip 2 and an opening 3, filled with oil or liquid parrafin 6 and including a device 10' according to a second preferred embodiment of the invention, placed on the lip 2 of the glass bottle 1.

The device 10' comprises a circular vessel 11' having a top 12' and a bottom 15' and an outwardly projecting lip 13' along the circumference of the vessel 11' at the top 12' thereof. However, it should be understood that any means to hold the device 11' in place on the lip 2 of the bottle 1 are acceptable. For example, the vessel 11' could be provided with a plurality of extensions at the periphery thereof which would rest on the lip 2 of the bottle 1.

The vessel 11', in this embodiment also extends downwardly into the opening 3 of the bottle 1, and is closed at the bottom 15' thereof and open at the top 12', defining a perfume-holding area 16'. The device 10' also comprises a central tubular element 17', made of metal or glass, although glass has a tendency to break easily, extending longitudinally through the center of the vessel 11' through which a wick 21' is inserted. A wick-supporting tube 19' may also be inserted through the central tubular element 17' to hold the wick in position. The central tubular element 17' is preferably further provided with a convex outwardly projecting flange 31', located at a given distance from the outwardly projecting lip 13' of the vessel 11'. This flange 31' prevents the perfume from being burned at the same time as the oil or paraffin. Indeed, the flange 31' acts to shield the flame of the wick 21 from the evaporations of the perfume and increase the diffusion of the perfume.

Preferably, the central tubular element 17' further has a bore 33' of slightly greater diameter that the diameter of the tubular element 17'. This permits the wick 21 to be located very close to the flange 31'. In use, the flame is thus almost in contact with the flange 31', which increases the heat communicated to the flange 31', and consequently to the vessel 11', thereby creating a more efficient diffusion for the perfume.

Preferably, an O-ring 35 is located around the central tubular element 17' at the bottom 15' of the vessel. Preferably, this O-ring 35 is made of neoprene and is resistant to heat and to the perfume.

In use, the perfume-holding area 16' is filled with perfume 29 in an amount determined by a user, either when it is placed on the lip 2 of the bottle 1, or removed from it. If the perfume-holding area 16' is filled when it is removed from the lip 2 of the bottle 1, the device 10' is then placed on the lip 2 of the glass bottle 1. When the wick 21 is lit, the heat generated by the flame heats the device 10', which, in turn, heats the perfume located in the perfume-holding area 16' thereby releasing a pleasing smell through the opening between the lip 13' of the device 10' and the flange 31' of the central tubular element 17'.

Thus, given the perfume-holding area 16', any number of perfumes may be poured into it to provide a pleasing smell. Furthermore, since the perfume is not mixed with the oil or liquid parrafin, the contents of the vessel 11' may be discarded and replaced with a different perfume should a user so wish. The device 10' also presents the additional advantage of not burning the perfume at the same time that the wick is lit. The pleasing smell is released only by the heat generated by the flame, through convection and diffusion.

In another variation, the vessel 11' may further be provided with another O-ring 37 so as to adequately seal the glass bottle 1 from the ambient air. To that effect, the vessel 11' is further provided with a groove 39 around the circumference of the vessel 11' in which the O-ring 37 may be installed. Thus, the air circulation required for proper operation of the device 10' is obtained through the central tubular element 17' as there is space between the inside of the tubular element 17' and the wick 21.

Figure 6:
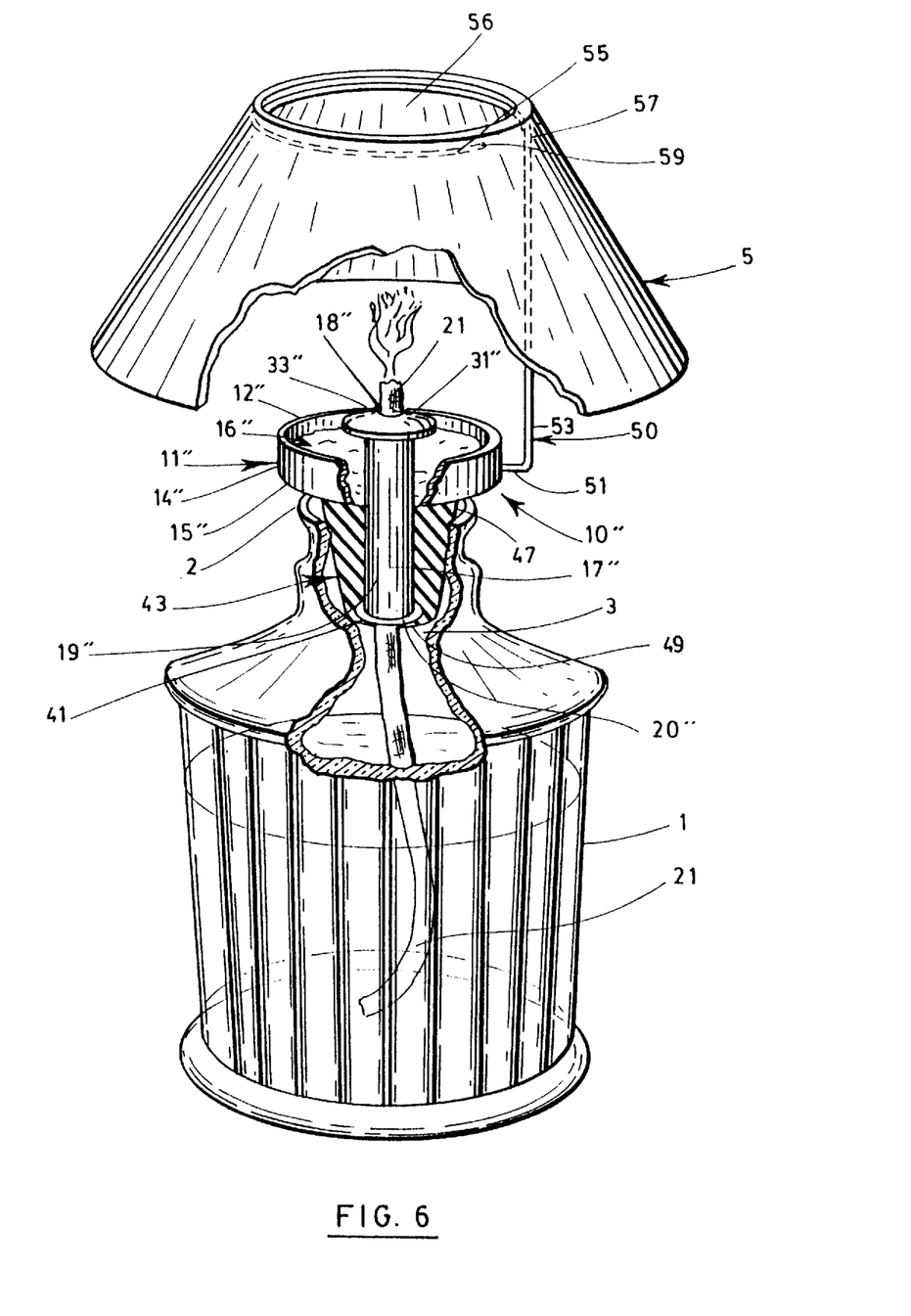
FIG. 6 is a schematic view of an oil lamp including a device according to a third preferred embodiment of the invention and including a lampshade.

FIG. 6 shows a device 10" according to a third preferred embodiment of the invention with an oil lamp 1, or glass bottle 1, and a lampshade 5.

The device 10" shown on FIG. 6 comprises a circular vessel 11" having a top 12" and a bottom 15" and a central tubular element 17" having a top 18" and a bottom 20". A wick 21 is inserted through the central tubular element 17". A wick-supporting tube 19" may also be inserted through the central tubular element 17" to hold the wick 21 in position.

Figures 7, 8, 9B:
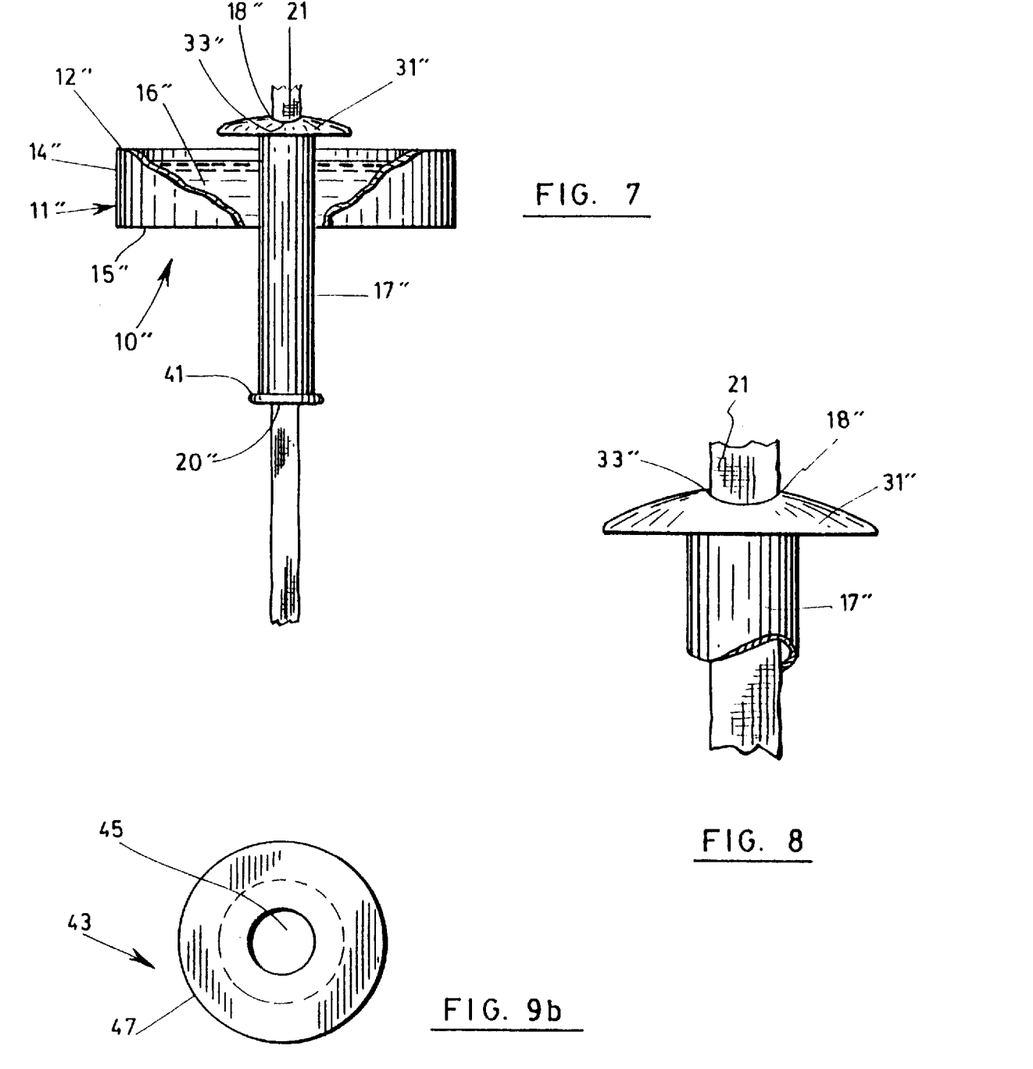
FIG. 7 is a perspective view of the device of FIG. 6.
FIG. 8 is an enlarged view of the top portion of the central tubular element of FIG. 7.
FIGS. 9a and 9b are, respectively, a side view and a top view of the resilient member for use with the device of FIG. 6.

The top 18" of the central tubular element 17" is preferably provided with an outwardly projecting flange 31" having a central bore 33". The outwardly projecting flange 31" is preferably convex in shape as better shown on FIGS. 6, 7 and 8. This avoids having the flame come in direct contact with the perfume, which would result in burning the perfume and not releasing a pleasing smell. The central bore 33" allows the wick 21 to be located as close as possible to the top 18" of the central tubular element 17" in order to more efficiently heat the device 10", the purpose of which will be detailed hereinafter.

The vessel 11" has an edge 14" having a given thickness. The top 12" of the vessel 11" has an inwardly, downwardly shaped cross-section similar to the shape of a saucer as shown on FIGS. 6, 7 and 8 defining a perfume-holding area 16".

The bottom 20" of the central tubular element 17" is provided with a rib 41. A resilient member 43 in the shape of an inverted truncated cone as shown on FIGS. 6, 7, 8 and 9a, has a central opening 45, a top 47 having a first diameter and a bottom 49 having a second diameter, the second diameter being smaller than the first diameter, is inserted around the central tubular element 17" with the top 47 of the resilient member 43 being located adjacent the bottom 15" of the vessel 11" and the bottom 49 of the resilient member 43 being located near the bottom 20" of the central tubular element 17". The rib 41 prevents the resilient member 43 from slipping off the central tubular element 17".

Figure 11:
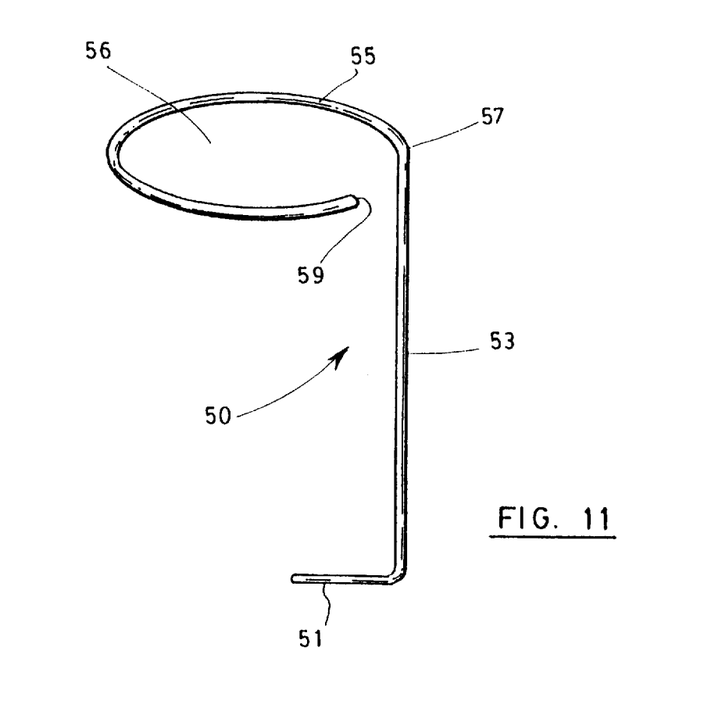
FIG. 11 is a top perspective view of the holder element.

The vessel 11" is provided with a holder element 50 having a first section 51 lying in a plane parallel to the bottom 15" of the vessel 11" fastened to the edge 14" thereof. Preferably, the first section 51 is soldered to the edge 14". The holder element 50 also has a second section 53 lying perpendicularly upwardly from the first section 51 and connected thereto and a circular portion 55 defining an opening 56, lying in a plane parallel to the first section 51, having a first end 57 connected to the second section 53 and a second end 59 located near the first end 57.

A wick 21, which may or may not include a wick-supporting tube 19, is inserted through the central tubular element 17" and projects upwardly at the top 18" of the element 17".

In use, the device 10" may be inserted into the opening 3 of an oil lamp 1 by wedging the resilient member 43 into the opening 3 as shown on FIG. 6. A few drops of perfume 29 can be poured into the perfume-holding area 16". A conventional lampshade 5 is placed on the circular portion 55 of the holder element 50. When the wick 21 is lit, the heat generated by the flame heats the device 10", thereby heating the perfume to release a pleasing smell.

This configuration thus permits the combination of an oil lamp with a lampshade for any type of vessel. Furthermore, perfume-holding area 16" permits the use of a perfume with the oil lamp to provide a pleasing smell.

This configuration is also quite secure, as the resilient member 43 shields the flame from the oil and remains wedged on the vessel should the oil lamp be inadvertently tipped over. The resilient member 43 also acts as an insulator between the lamp and the device, which otherwise could overheat and could cause breakage of the oil lamp itself. Preferably, the resilient member 43 is made of rubber, cork, neoprene or any other suitable material.

It should be noted that the device 10" may be used in combination with any type of container since the truncated shape of the resilient member 43 allows it to be inserted into a variety of opening diameters. It should also be recognized that changing the resilient member 43 to a larger version or a smaller version allows the use of the device 10" not only with containers having opening diameters within the first and second diameters of any particular resilient members 43, but with containers having a far greater range of diameters.

Figure 9A:
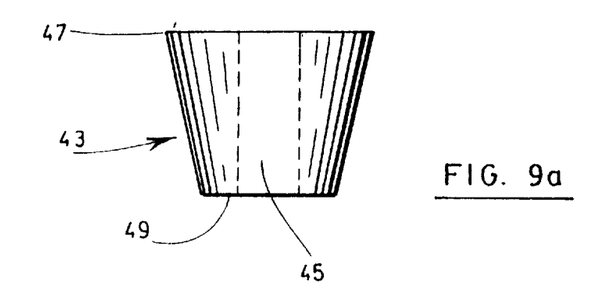
Figure 12:
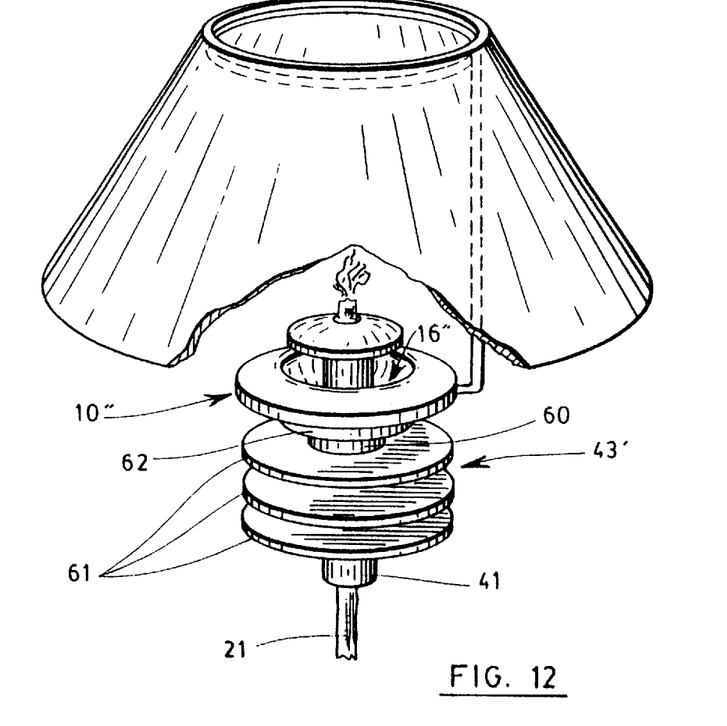
FIG. 12 is a perspective view of the device including a variant to the resilient member, where the resilient member is provided with fins.
Figure 13:
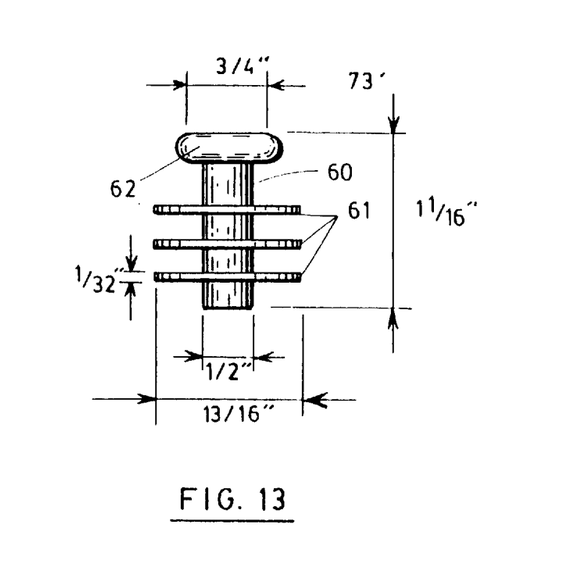
FIG. 13 is a cross-sectional view of the resilient member of FIGS. 12 and 13.
Figure 14:
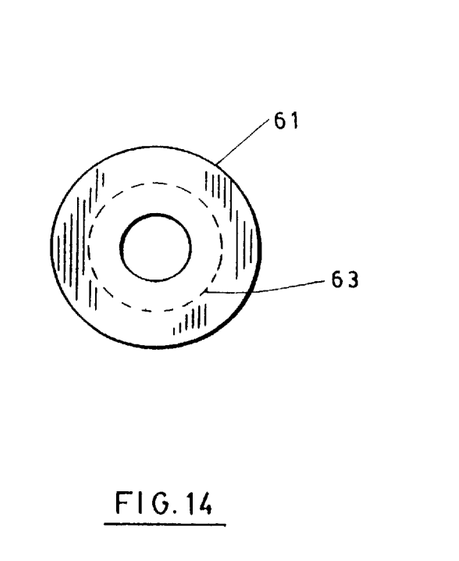
FIG. 14 is a plan view of one of the fins of the resilient member shown in FIG. 12.

Instead of using a resilient member 43 shaped as a truncated cone as shown in FIGS. 6 and 9a, use can alternatively be made of a resilient member 43' as shown in FIGS. 12 to 14, comprising a hollow tube 60 with a knurled head 62 and a set of annular fins 61 made of resilient plastic material. The knurled head 62 makes the tube 60 easy to grip. As is shown in FIG. 14, the fins 61 may be provided with tearing lines 63 to adjust their size if need be.

This other resilient member 43' provides for a greater flexibility in inserting the device 10" in lamps having a greater variation in their opening diameters without having to replace the resilient member 43 with another having different dimensions. The resilient member 43' also ensures a better anchoring of the device into the neck or opening 3 of the lamp 1. The fins 61, made of plastic material, are resistant to the perfumes and/or oil and make the device easy to remove in order to fill up the lamp 1 whenever necessary. The fins 61 also permit to keep the device stable even when the lamp is shaken and/or frequently handled.

Figure 15:
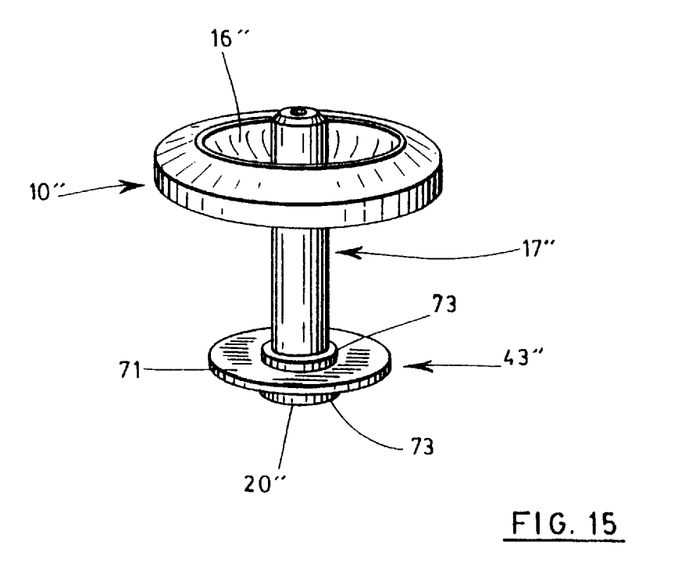
FIG. 15 is a cross-sectional view of the device including another variant to the resilient member, where the resilient member consists of a washer.

Alternatively, as shown on FIG. 15, the resilient member 43" may include a single washer 71 inserted near the bottom of the central tubular element 17". In order to hold the washer 71 in position, a pair of ribs 73 are provided near the bottom 20" of the central tubular element 17" and the washer is held in position between each rib of the pair of ribs 73.

It should be noted that the perfume to be used with the present invention should not be overly concentrated so as to overwhelm a user, nor should it contain alcohol, as it would evaporate too quickly.

Preferably, the vessel 11" is made of brass to permit adequate heat conductivity, but could also be made of any other suitable material such as glass, although glass has a tendency to break more easily.

For the first and second preferred embodiments, the vessel 11 and 11' preferably have a height of 35 mm and a diameter of 20 mm, thus can be used with oil lamps 1 having an opening 3 greater than 20 mm.

Figure 10:
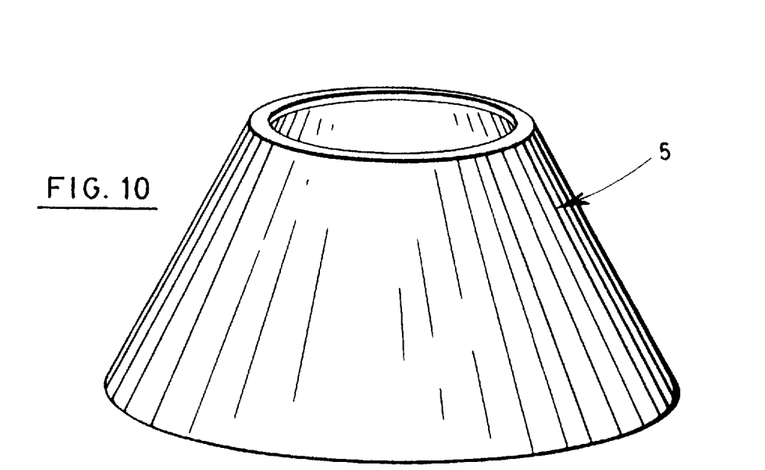
FIG. 10 is a top perspective view of a conventional lampshade for use with the invention.

It should also be noted that the holder element 50 and the lampshade 5 can also be used with the first and second embodiments, provided that the outwardly projecting lip 13 has a thickness great enough to permit the soldering of the holder element 50 to it.

It should also be noted that the perfume used with the present invention does not have to be liquid. Indeed, it is possible to insert the perfume into wax or paraffin, which, at room temperature, is solid, but when heated by the wick liquefies and thus releases the scent of the perfume.

Although the present invention has been explained hereinabove by way of a preferred embodiment thereof, it should be pointed out that any modifications to this preferred embodiment within the scope of the appended claims is not deemed to alter or change the nature and scope of the present invention.

We claim:

1. A device for use with an oil lamp to allow the diffusion of the scent of a perfume, said oil lamp having a lip and an opening of a predetermined diameter, said device comprising:
   a circular vessel having a top, a bottom, a center, a circumference and being closed at the bottom and open at the top thereof, thereby defining a perfume-holding area;
   a central tubular element having a top and a bottom extending longitudinally through the center of said vessel, said central tubular element including a wick;
   means to hold in position said device on said lip of said oil lamp and over said opening;
   said means to hold in position include an outwardly projecting flange at the top of said vessel, and
   said vessel extends into said opening a predetermined distance; a ring-like element having a central opening adapted to be inserted around said central tubular element at the top thereof such that said central tubular element projects upwardly from said ring-like element, said ring-like element having a diameter adapted to rest on said outwardly projecting lip of said device, said ring-like element being provided with openings to permit air flow between said perfume-holding area and ambient air.

2. A device according to claim 1, wherein said ring-like element has a periphery and said openings are semi-circular and located at said periphery.

3. A device according to claim 1, wherein said ring-like element has a body and said openings are located in said body.

4. A device for use of an oil lamp to allow the diffusion of the scent of a perfume, said oil lamp having a lip and an opening of a predetermined diameter, said device comprising: a circular vessel having a top, a bottom, a center, a circumference and being closed at the bottom and open at the top thereof, thereby defining a perfume holding area; a central tubular element having a top and a bottom extending longitudinally through the center of said vessel, said central tubular element including a wick; means to hold in position said device on said lip of said oil lamp and over said opening; said means to hold in position including an outwardly projecting flange at the top of said vessel, and wherein said central tubular element is provided with an outwardly projecting flange at the top end thereof.

5. A device according to claim 4, wherein said outwardly projecting flange of said central tubular element is convex.

6. A device according to claim 4, wherein said tubular element is further provided with a central bore, whereby said wick can be located adjacent said outwardly projecting flange.

7. A device according to claim 4, wherein said central tubular element is further provided with a first O-ring at a junction between the bottom of the central tubular element and said bottom of said vessel.

8. A device according to claim 4, wherein said vessel further has a periphery and is provided with a groove at said periphery of said vessel, and wherein said groove is further provided with a second O-ring, whereby when said device is inserted into the opening of said oil lamp, said second O-ring seals said oil lamp from ambient air.

9. A device according to claim 4, wherein:
   said outwardly projecting flange is convex;
   said central tubular element is further provided with a central bore, whereby said wick can be located adjacent said outwardly projecting flange;
   said central tubular element is further provided with a first O-ring at a junction between the bottom of the central tubular element and said bottom of said vessel; and
   said vessel further has a periphery and is provided with a groove at said periphery of said vessel, and wherein said groove is further provided with a second O-ring, whereby when said device is inserted into the opening of said oil lamp, said second O-ring seals said oil lamp from ambient air.

10. A device for use with an oil lamp to allow the diffusion of the scent of a perfume, said oil lamp having a lip and an opening of a predetermined diameter, said device comprising:
    a circular vessel having a top, a bottom, a center, a circumference and being closed at the bottom and open at the top thereof, thereby defining a perfume-holding area;
    a central tubular element having a top and a bottom extending longitudinally through the center of said vessel, said central tubular element including a wick; and
    means to hold in position said device on said lip of said oil lamp and over said opening;
    said central tubular element projects downwardly into said opening and upwardly above said vessel;
    said means to hold the device in position consist of said vessel having a diameter greater than the diameter of said opening and a portion of the central tubular element between the bottom of said central tubular element and the bottom of said vessel being provided with a resilient member; and
    said vessel has an edge and a predetermined thickness, the top of said vessel having a cross-section that is inwardly and downwardly shaped.

11. A device according to claim 10, wherein said top of said central tubular element is provided with an outwardly projecting flange.

12. A device according to claim 11, wherein said outwardly projecting flange of said central tubular element is convex.

13. A device according to claim 10, wherein:
    said bottom of said central tubular element is provided with a rib, and said resilient member is in the shape of an inverted truncated cone, having a central opening, a top having a first diameter and a bottom having a second diameter, where the second diameter is smaller than the first diameter, the resilient member being inserted around said central tubular element with the top of the resilient member being located adjacent the bottom surface of said vessel, and the bottom of the resilient member being located near the bottom of said central tubular element, such that said rib prevents said resilient member from slipping off the central tubular element.

14. A device according to claim 10, wherein:
    said bottom of said central tubular element is provided with a pair of spaced apart annular ribs and said resilient member is a washer located between each rib of said pair of ribs.

15. A device according to claim 10, wherein:
    said resilient member comprises a hollow tube having a knurled head and at least one set of annular fins, inserted around said central tubular element.

16. A device according to claim 13, wherein said top of said central tubular element is provided with an outwardly projecting flange.

17. A device according to claim 16, wherein said outwardly projecting flange is convex.

18. A device according to claim 10, wherein:

said top of said central tubular element is provided with a convex outwardly projecting flange;

said bottom of said central tubular element is provided with a rib, and said resilient member is in the shape of an inverted truncated cone, having a central opening, a top having a first diameter and a bottom having a second diameter, where the second diameter is smaller than the first diameter, the resilient member being inserted around said central tubular element with the top of the resilient member being located adjacent the bottom surface of said vessel, and the bottom of the resilient member being located near the bottom of said central tubular element, such that said rib prevents said resilient member from slipping off the central tubular element.

19. A device for use with an oil lamp to allow the diffusion of the scent of a perfume, said oil lamp having a lip and an opening of a predetermined diameter, said device comprising:

a circular vessel having a top, a bottom, a center, a circumference and being closed at the bottom and open at the top thereof, thereby defining a perfume-holding area;

a central tubular element having a top and a bottom extending longitudinally through the center of said vessel, said central tubular element including a wick; and means to hold in position said device on said lip of said oil lamp and over said opening; a holder element fastened to said vessel and a lampshade resting on said holder element.

20. A device according to claim 1, wherein said device further includes a holder element fastened to said vessel and a lampshade resting on said holder element.

21. A device according to claim 9, wherein said device further includes a holder element fastened to said vessel and a lampshade resting on said holder element.

22. A device according to claim 18, wherein said device further includes a holder element fastened to said vessel and a lampshade resting on said holder element.

23. A device according to claim 19, wherein said holder element has:

a first section lying in a plane parallel to the bottom of said vessel, said first section being fastened to the edge of said vessel;

a second section lying perpendicularly upwardly from said first section and connected thereto;

a circular portion defining an opening, lying in a plane parallel to said first section, having a first end connected to said second seection and a second end located adjacent said first end.

24. A device according to claim 20, wherein said holder element has:

a first section lying in a plane parallel to the bottom of said vessel, said first section being fastened to the edge of said vessel;

a second section lying perpendicularly upwardly from said first section and connected thereto;

a circular portion defining an opening, lying in a plane parallel to said first section, having a first end connected to said second seection and a second end located adjacent said first end.

25. A device according to claim 21, wherein said holder element has:

a first section lying in a plane parallel to the bottom of said vessel, said first section being fastened to the edge of said vessel;

a second section lying perpendicularly upwardly from said first section and connected thereto;

a circular portion defining an opening, lying in a plane parallel to said first section, having a first end connected to said second seection and a second end located adjacent said first end.

26. A device according to claim 22, wherein said holder element has:

a first section lying in a plane parallel to the bottom of said vessel, said first section being fastened to the edge of said vessel;

a second section lying perpendicularly upwardly from said first section and connected thereto;

a circular portion defining an opening, lying in a plane parallel to said first section, having a first end connected to said second section and a second end located adjacent said first end.

27. A device according to claim 4, wherein said device further includes a holder element fastened to said vessel and a lamp shade resting on said holder element.

28. A device according to claim 10, wherein said said device further includes a holder element fastened to said vessel and the lamp shade resting on said holder element.

* * * * *